United States Patent
Oskin et al.

(10) Patent No.: US 8,231,658 B2
(45) Date of Patent: Jul. 31, 2012

(54) INTRODUCER DEVICE WITH LOCKING ADAPTOR

(75) Inventors: Christopher Oskin, Grafton, MA (US); Brian MacLean, Westford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 898 days.

(21) Appl. No.: 12/270,390

(22) Filed: Nov. 13, 2008

(65) Prior Publication Data

US 2009/0124858 A1 May 14, 2009

Related U.S. Application Data

(60) Provisional application No. 60/987,863, filed on Nov. 14, 2007.

(51) Int. Cl.
*A61B 17/70* (2006.01)
(52) U.S. Cl. ........................................ 606/272; 600/125
(58) Field of Classification Search .................... 70/118, 70/129; 600/125; 606/272; 439/744–746
See application file for complete search history.

(56) References Cited

U.S. PATENT DOCUMENTS

| 4,254,762 | A | | 3/1981 | Yoon |
| 5,151,101 | A | * | 9/1992 | Grossi et al. ................... 606/46 |
| 5,630,799 | A | | 5/1997 | Beiser et al. |
| 6,428,538 | B1 | | 8/2002 | Blewett et al. |
| 2002/0072652 | A1 | | 6/2002 | Berci et al. |
| 2007/0049929 | A1 | * | 3/2007 | Catanese et al. ................ 606/46 |
| 2007/0077821 | A1 | * | 4/2007 | Pilavdzic ................. 439/620.21 |
| 2007/0077827 | A1 | * | 4/2007 | Bonde et al. .................. 439/745 |
| 2007/0225562 | A1 | * | 9/2007 | Spivey et al. ................. 600/121 |
| 2008/0051735 | A1 | * | 2/2008 | Measamer et al. ............ 604/265 |

FOREIGN PATENT DOCUMENTS

WO 0195810 12/2001

\* cited by examiner

*Primary Examiner* — Nicholas Lucchesi
*Assistant Examiner* — Gerald Landry, II
(74) *Attorney, Agent, or Firm* — Fay Kaplun & Marcin, LLP

(57) ABSTRACT

Introducer Device comprises (a) Housing including (1) Housing Lumen sized and shaped to slidably receive a visualization device therein and (2) Slot sized to receive therein a projection extending from visualization device received in Lumen radially away from Lumen; (b) Sheath extending distally from handle and being sized and shaped for insertion through a natural body opening into a hollow body organ, Sheath including a fluid delivery lumen delivering heated fluid to the organ and a fluid return lumen withdrawing the fluid after it has been circulated through the organ; (c) Connector including Connector Lumen aligned with Lumen and sized and shaped to slidably receive therein visualization device; (d) Locking arrangement movably coupled to Housing, movement relative to the housing opening and closing Slot; and (e) Adjustment mechanism moving Connector relative to Housing to adjust distance between a proximal end of Connector Lumen and a distal end of Sheath.

26 Claims, 3 Drawing Sheets

INTRODUCER DEVICE WITH LOCKING ADAPTOR

PRIORITY CLAIM

This application claims the priority to the U.S. Provisional Application Ser. No. 60/987,863, entitled "INTRODUCER DEVICE WITH LOCKING ADAPTOR," filed Nov. 14, 2007. The specification of the above-identified application is incorporated herewith by reference.

BACKGROUND

Although hysterectomy is generally an effective treatment for menorrhagia, less invasive procedures are often preferable as they reduce side effects, hospital stays and procedural and post-operative discomfort. These less invasive procedures may involve ablating the endometrial lining using radio-frequency energy, laser, heated fluid, etc.

It is often desired to monitor progress of the procedure using a visualization device. However, conventional inter-uterine ablation systems either may not support use of a visualization device or support only the use of a manufacturer/model-specific visualization device. Thus, the inter-uterine ablation systems and/or visualization devices available for ablating the endometrial lining may be limited.

SUMMARY OF THE INVENTION

The present invention is directed to an introducer device for a thermal ablation system comprising a housing including a housing lumen sized and shaped to slidably receive a visualization device therein, the housing further including a slot sized to receive therein a projection extending from a visualization device received in the housing lumen radially away from the housing lumen and a sheath extending distally from the handle, the sheath being sized and shaped for insertion through a natural body opening into a hollow body organ, the sheath including a fluid delivery lumen delivering heated fluid to the organ and a fluid return lumen withdrawing the fluid after it has been circulated through the organ in combination with a connector including a connector lumen aligned with the housing lumen and sized and shaped to slidably receive therein a visualization device and a locking arrangement movably coupled to the housing, movement of the locking arrangement relative to the housing opening and closing the slot. An adjustment mechanism moves the connector relative to the housing to adjust a distance between a proximal end of the connector lumen and a distal end of the sheath.

The present invention is further directed to a coupling arrangement for detachably coupling a visualization device to a medical device, the arrangement comprising a housing including a housing lumen extending therethrough, the housing lumen being sized and shaped to slidably receive a visualization device therein and a connector movably connected to the housing to adjust a distance between a proximal end of the connector and a distal end of the device, the connector defining a connector lumen in alignment with the housing lumen and being sized and shaped to slidably receive a visualization device therein in combination with a locking arrangement securing the visualization device at a desired position within the housing.

DETAILED DESCRIPTION

Figure 1:
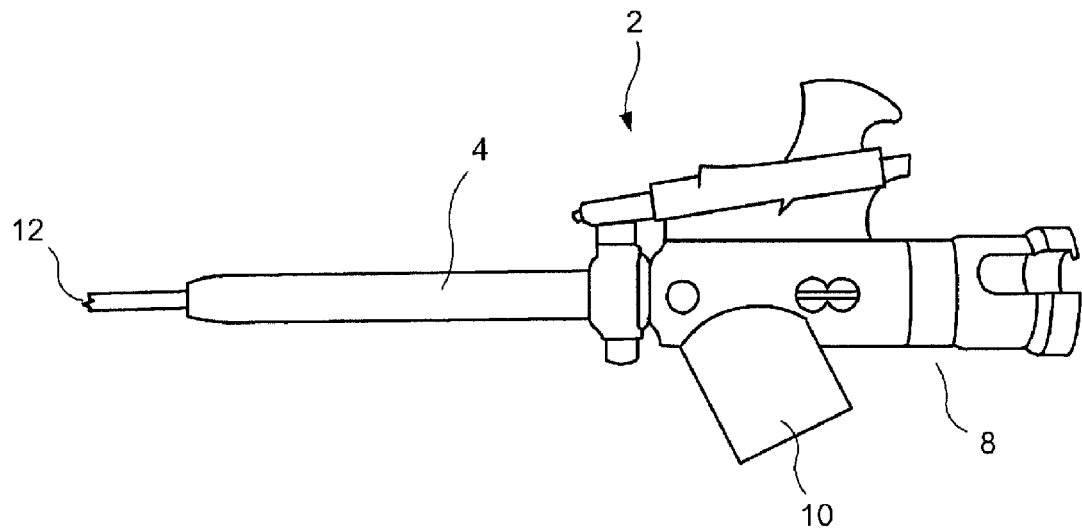
FIG. 1 shows an exemplary embodiment of an introducer device according to the present invention.

The present invention may be further understood with reference to the following description and to the appended drawings, wherein like elements are referred to with the same reference numerals. The present invention relates to a locking adaptor for use with an introducer device which may be part of a thermal ablation system used for thermally ablating tissue lining an inner surface of a hollow organ. In particular, the thermal ablation system may be used for ablating the endometrial lining of the uterus. The locking adaptor according to the present invention may allow the introducer device to be coupled to visualization devices of different sizes and made by different manufacturers. Those skilled in the art will understand that, although the invention is described with specific reference to the treatment of the lining of the uterus, the same device may be used with minor modifications (e.g., changing the diameter, length and any curve of the device) to treat the interiors of a wide variety of hollow organs accessed via either a naturally occurring body orifice or a surgically created opening.

FIG. 1 shows an exemplary embodiment of an introducer device 2 according to the present invention delivering heated fluid to the uterus for circulation therethrough and ablation of the endometrial lining. The introducer device 2 comprises a sheath 4 for introducing the fluid into and withdrawing the fluid from the uterus, an ergonomic grip 6 and a scope adaptor 8 for detachably receiving a visualization device. In one exemplary embodiment, the introducer device 2 is manufactured from low-cost materials and useable as a single-use device. Alternatively, if manufactured from more durable materials, the introducer device 2 may be made reusable after sterilization. During the ablation procedure, the grip 6 and the scope connector 8 remain outside the body, while the sheath 4 is inserted into the uterus via the cervix or into another hollow organ via a naturally occurring body orifice or a surgically created opening.

The grip 6 includes a handle 10 so that the introducer device 2 can be held and manipulated with a single hand leaving the other hand free to adjust the visualization device, manipulate the patient's anatomy, etc. Fluid delivery and return lumens for injecting heated fluid to and withdrawing fluid from the uterus, pass through a bottom portion of the grip 6 for coupling to fluid delivery and return lumens (not shown) in the introducer device 2. As would be understood by those skilled in the art, the heated fluid preferably has a temperature of approximately 85-90 EC when it is delivered to the uterus and may be circulated through the uterus for approximately ten minutes. Those of skill in the art will understand that the temperature and duration of the circulation of the heated fluid may vary as needed to attain a desired level of treatment of the target tissue.

The fluid delivery and return lumens terminate at a distal end 12 of the sheath 4 which extends distally from the grip 6. In use, the sheath 4 is inserted through the cervix into the uterus for the delivery of the heated fluid thereto. Maintenance of a fluid-tight seal during the ablation procedure ensures that proper fluid pressure is maintained within the uterus to ablate the endometrial lining and prevents the escape of heated fluids from the uterus where they may injure non-targeted tissue. The elasticity of the cervix may be relied on to create a fluid-tight seal around the sheath 4 or, in another embodiment, a cervical seal may be disposed around a portion of the sheath 4 which, during use, is received within the cervix to enhance/maintain the fluid-tight seal therearound. The cervical seal may be, for example, a radially expandable mini-sheath wrapped around the distal portion of the sheath 4 which, when expanded, exerts pressure radially outward against the cervix. The elasticity of the walls of the cervix exert a resisting pressure against the pressure exerted by the mini-sheath enhancing the fluid-tight seal around the sheath 4. In another exemplary embodiment, the cervical seal is formed as a snare loop which encircles the cervix and pulls it radially inward around the sheath 4 as would be understood by those skilled in the art.

The scope adaptor 8 is coupled to a proximal end of the grip 6 and provides a point for attachment of the visualization device (e.g., a hysteroscope, an endoscope, a cytoscope, etc.) to the introducer device 2. As would be understood by those skilled in the art, these visualization devices generally comprise an elongated tube with a vision system including, for example, an illumination element and an image capturing element such as a fiber optic array or CCD device at a distal end thereof. The visualization device is passed distally through a visualization lumen in the introducer device 2 and extended from the distal end 12 of the sheath 4 so that the operator may visually monitor insertion of the sheath 4 into the uterus and the progress of the ablation procedure.

Figure 2:
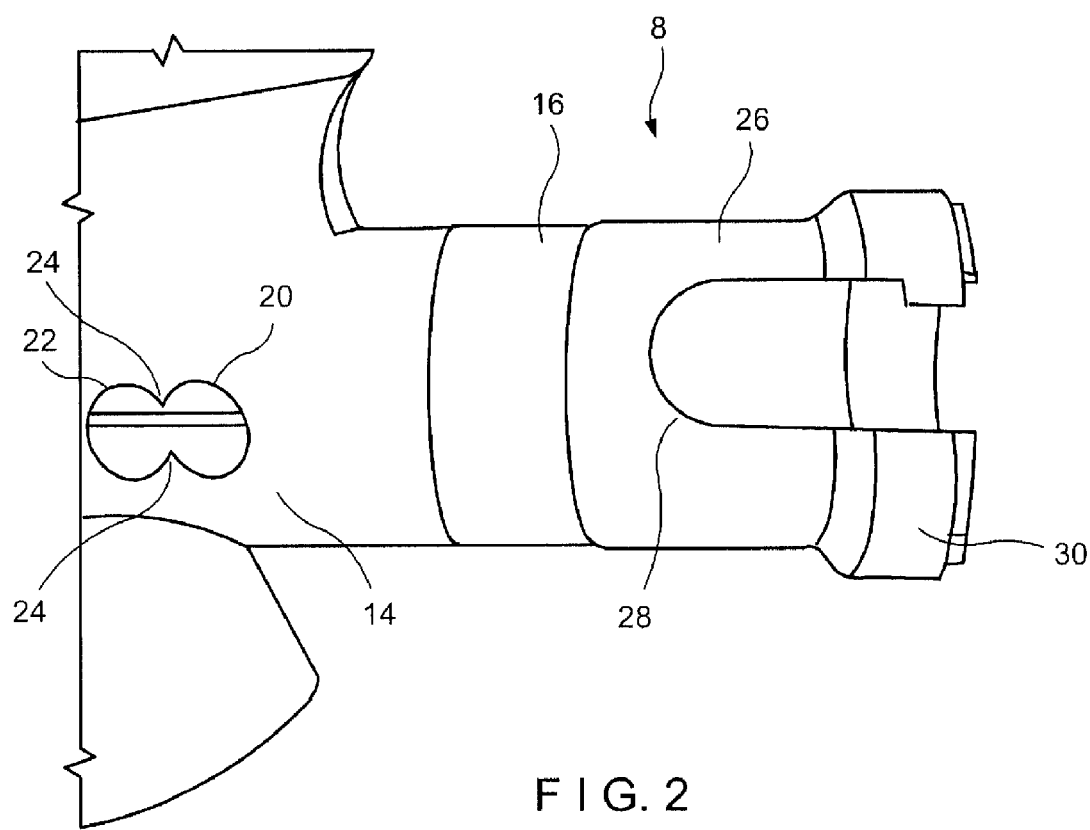
FIG. 2 shows an exemplary embodiment of a scope adaptor according to the present invention.

As shown in FIG. 2, an exemplary scope adaptor 8 comprises a length adaptor 14, a joint 16 and a scope connector 18. The length adaptor 14 utilizes an interconnection between the scope adaptor 8 and the grip 6 to selectively elongate/shorten the introducer device 2 to accommodate visualization devices of various lengths. In the exemplary embodiment, the grip 6 includes proximal and distal cavities 20, 22 formed in a body thereof which receive a projection (not shown) formed on a distal portion of the scope adaptor 8 which is inserted into and longitudinally moveable relative to a proximal end of the grip 6. Positioning the projection in the proximal cavity 20 elongates the introducer device 2 to accommodate visualization devices having a first length, whereas positioning the projection in the distal cavity 22 shortens the introducer device 2 to accommodate visualization devices having a second length less than the first length. In the exemplary embodiment, each of the proximal and distal cavities 20, 22 is formed to prevent the projection from moving proximally or distally thereout of (i.e., sized and shaped to tightly receive the projection). For example, as shown in FIG. 2, partially-formed retainers 24 may project into an inter-cavity space, requiring a voluntary, manual force to move the projection between the proximal and distal cavities 20, 22. Those of skill in the art will understand that any number of cavities may be formed on the grip 6 for accommodating visualization devices with various lengths. In addition, other mechanisms may be utilized for selectively elongating/shortening a length of the introducer device 2 which may include, but are not limited to, ratchet mechanisms, rack and pinion assemblies, worm gears, automated assemblies, etc.

The joint 16 according to this embodiment is formed as a collar rotatably coupling the scope connector 18 to the grip 6. Allowing the scope connector 18 to rotate relative to the grip 6 allows an operator to freely manipulate the introducer device 2 without fear of having movement restricted or entangled by wires of the visualization device. Those of skill in the art will understand that in other exemplary embodiments, the grip 6 and the scope connector 8 may be integrally formed or otherwise rigidly coupled to one another. In such embodiments, the joint 16 is not be utilized.

The scope connector 18 includes a body portion 26 defining a lumen therethrough which is shaped and sized to slidably receive an insertion section of the visualization device therein and to pass the insertion section therethrough to the visualization lumen of the device 2. In the exemplary embodiment, the body portion 26 is substantially cylindrically shaped and is open at its distal end to a proximal end of the visualization lumen while its proximal end is open to receive the insertion section. The distal end of the connector 18 may be rotatably coupled to the joint 16. A channel 28 may be formed in a sidewall of the body portion 26 for receiving the connector for the scope light optics & camera referred to by some as the light pipe. The scope connector 18 preferably includes internal features incorporating elements of the distal ends of several types of scopes so that any of these types of scopes may be received therein. However, those skilled in the art will understand that such adaptability is optional and the connector 18 may alternatively be custom designed for one type of scope.

A locking ring 30 may be coupled to the proximal end of the scope connector 18 to lock the connector for the scope light and optics within the channel 28, ensuring that the visualization device remains coupled to the introducer device 2 in a desired position relative thereto. In the exemplary embodiment, an outer surface of the proximal end of the scope connector 18 has one or more ridges (threads, etc.) formed thereon which mate with corresponding grooves on an inner surface of the locking ring 30. Thus, the locking ring 30 is rotatably coupled to the proximal end of the scope connector 18.

Figure 5:
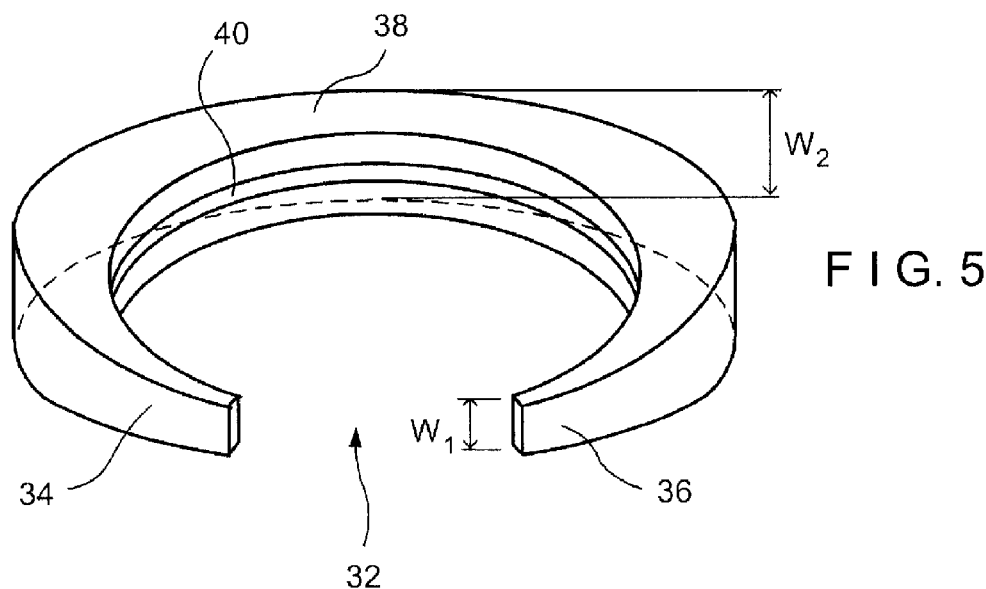
FIG. 5 shows an exemplary embodiment of a locking ring according to the present invention.

The locking ring 30, shown in FIG. 5, may be formed as a substantially C-shaped structure having a channel 32 separating two open ends 34, 36 thereof. The channel 32 preferably has a width substantially equivalent to a width of the channel 28 of the scope connector 18. In the exemplary embodiment, each of the open ends 34, 36 has a predetermined width $W_1$ which increases gradually along a circumference of the locking ring 30 to a closed portion 38 (opposite the open ends 34, 36) having a width $W_2$. The gradual increase in width allows the locking ring 30 to gradually compress the connector of the scope against a distal end of the channel 28, maintaining the visualization device at a desired position within the scope connector 18, while supporting scopes which vary not only in overall length but also in the distance between the scope connector and the distal portion of the scope handle. Where both open ends 34, 36 have the width $W_1$, the locking ring 30 may be rotated in either direction to lock the scope therein while a uni-directional locking ring 30 may be formed where only one of the open ends 34, 36 has the width $W_1$. Those skilled in the art will understand that the width of the locking ring 30 is inconsequential so long as a distal surface of the ring 30 is oriented so that, upon rotation of the ring 30 away from a position in which the channel 28 and the channel 32 are aligned, a distal surface of the portion of the ring 30 passing over the channel 28 moves distally, forcing any portion of the scope protruding from the channel 28 to move distally. Furthermore, those skilled in the art will understand that the locking ring 30 may include any number of ergonomic features such as tabs, projections, textured surfaces, etc. to aid in closing the ring 30 in either direction. In addition, the ring 30 may be thickened or otherwise reinforced to increase its locking strength.

A groove 40 for mating with a ridge (not shown) on the proximal end of the scope connector 18 is formed on an inner surface of the locking ring 30 and extends along the circumference thereof. The groove 40 allows the locking ring 30 to be rotated relative to the scope connector 18. In an exemplary embodiment, the ridge includes transverse projections disposed at predetermined spaces therealong which mate with corresponding transverse inlets formed on the groove 40. As the locking ring 30 is rotated relative to the scope connector 18, the operator may hear clicks when projections mate with the inlets, providing audible feedback that the locking ring 30 will not freely rotate around the scope connector 18. Thus, the locking ring 30 may be maintained in a static position relative to the scope connector 18, ensuring that the channel 28 will remain sealed by the locking ring 30 while the operator manipulates the visualization device and/or the introducer device 2.

Figure 3:
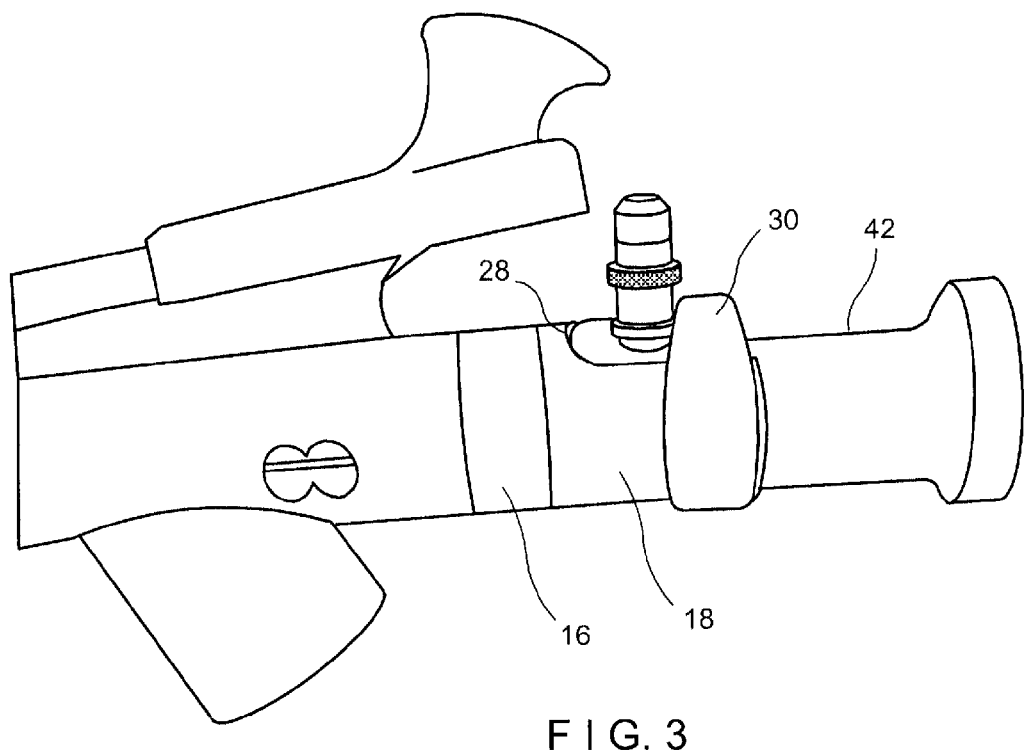
FIG. 3 shows an exemplary embodiment of a scope coupled to a scope adaptor according to the present invention.
Figure 4:
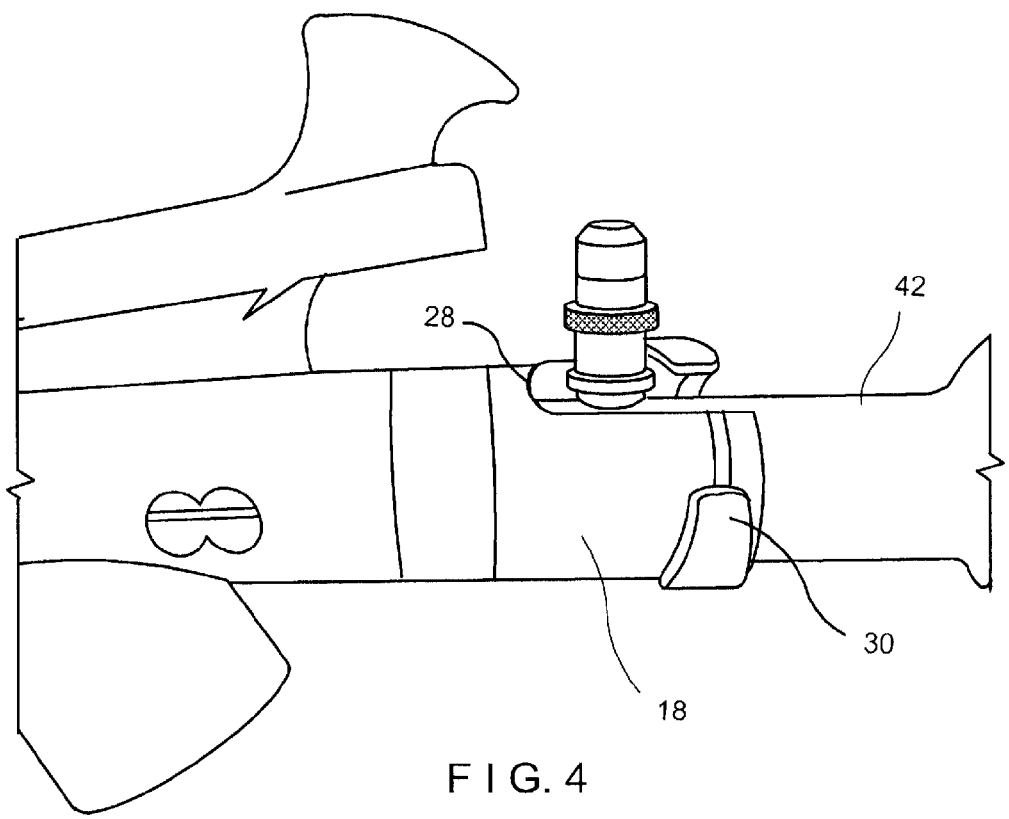
FIG. 4 shows an exemplary embodiment of a scope locked to an introducer device according to the present invention.

FIGS. 3 and 4 show a visualization device coupled to an introducer device 2 in accordance with the present invention. When the locking ring 30 is in an unlocked position (FIG. 3), the channel 32 is aligned with the channel 28 on the scope connector 18 and the visualization device (e.g., a hysteroscope 42) may be inserted into the introducer device 2 until a visualization element of the hysteroscope 42 extends at least to the distal end 12 of sheath 4 providing a desired field of view. To ensure that the visualization element obtains the desired field of view, the length adaptor 14 is utilized ensure that, the visualization device is maintained at a desired depth of insertion within the introducer device 2. That is, as the length of the visualization lumen is shorter than a length of the visualization device by a known amount, the extension of the scope connector 18 is adjusted so that the combined length of the connector 18 and the visualization lumen are shorter than a length of the insertion section by a desired length of extension of the distal end of the insertion section from the device 2.

After the length of the adaptor 14 has been properly adjusted, the visualization device (e.g., hysteroscope 42) may be locked into the channel 28 using the locking ring 30. In the exemplary embodiment, the locking ring 30 is rotated relative to the scope connector 18 between open and closed positions to seal the channel 28 and lock the scope 42 therein. As the locking ring 30 is rotated, the width of the locking ring 30 compresses the scope connector toward a distal end of the channel 28, as shown in FIG. 4. Alternatively, the locking ring 30 may simply be rotated across a proximal end of the channel 28 to close this end. In such an embodiment, the locking ring 30 preferably has a substantially uniform width.

Figure 6:
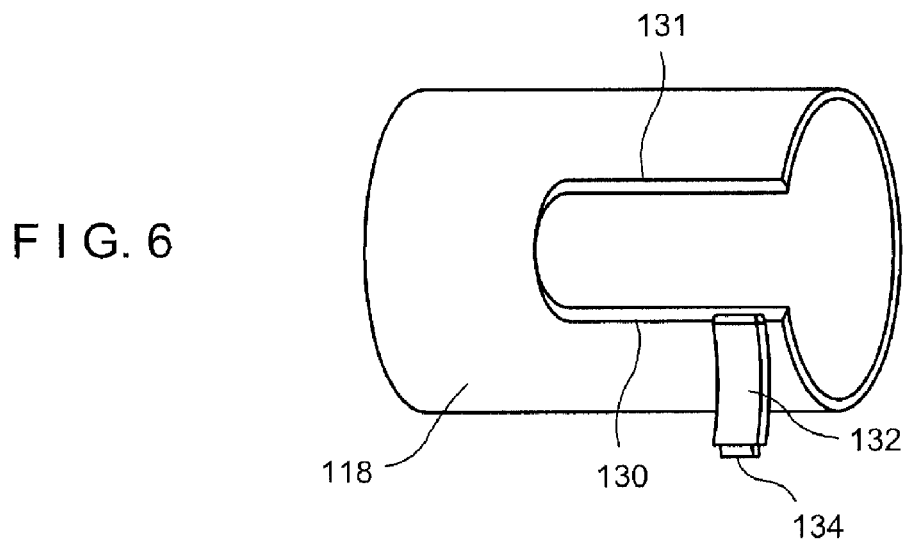
FIG. 6 shows an exemplary embodiment of a hinged latch for a scope adaptor in an open state according to the present invention.
Figure 7:
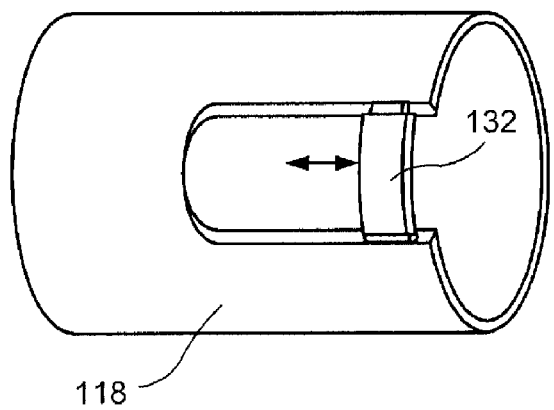
FIG. 7 shows an exemplary embodiment of a hinged latch for a scope adaptor in a closed state according to the present invention.

FIGS. 6 and 7 show an alternative exemplary embodiment of a scope adaptor 100 according to the present invention. The scope adaptor 100 includes a scope connector 118 structurally similar to the scope connector 18. That is, the scope connector 118 is substantially cylindrically shaped, although those skilled in the art will understand that this shape may be altered as necessary to accommodate scopes of different shapes, and includes an open proximal which receives the visualization device and a channel 128 which receives the scope part. In this embodiment, the channel 128 may include slots 130, 131 along its respective lengths. A latch 132 having a length at least as great as a width of the channel 128 is hinged adjacent to the slot 130 with a hinge of the latch 132, for example, slidably disposed in the slot 130 so that the latch 132 may rotate relative to the slot 130 and slide therein. An end of the latch 132 opposite the hinge includes a connector such as a tab 134 which may be detachably and slidably disposed in the slot 131 shown in FIG. 7. Thus, after the hysteroscope 42 has been inserted into the scope connector 118, the latch 132 may be folded over the channel 128 and coupled to the slot 131 using the tab 134. The latch 132 may then slide distally within the channel 128, compressing the scope connector 18 against the distal end of the channel 128. In another exemplary embodiment, the slots 130, 131 include defined positions for the hinge and tab 134, respectively, requiring voluntary, manual force to move the latch 132 within the channel 128. This embodiment may utilize, for example, a ratchet slide to ensure that the latch 132 does not freely move within the channel 128 and provide audible feedback (e.g., clicks) indicating that the latch 132 is retained by the slot 131.

The present invention has been described with reference to specific exemplary embodiments. Those skilled in the art will understand that changes may be made in details, particularly in matters of shape, size, material and arrangement of parts. For example, the invention is not limited to methods and devices for the thermal ablation of the uterine lining. Accordingly, various modifications and changes may be made to the embodiments. The specifications and drawings are, therefore, to be regarded in an illustrative rather than a restrictive sense.

What is claimed is:

1. An introducer device for a thermal ablation system, comprising:
    a housing including a housing lumen sized and shaped to slidably receive a visualization device therein, the housing further including a slot extending therethrough from an interior surface defining the housing lumen to an exterior surface thereof, the slot sized to receive therein a projection extending from a visualization device received in the housing lumen radially away from the housing lumen and past the exterior surface of the housing;
    a sheath extending distally from a handle, the sheath being sized and shaped for insertion through a natural body opening into a hollow body organ, the sheath including a fluid delivery lumen delivering heated fluid to the organ and a fluid return lumen withdrawing the fluid after it has been circulated through the organ;
    a connector including a connector lumen aligned with the housing lumen and sized and shaped to slidably receive therein the visualization device;
    a locking arrangement movably coupled to the housing, movement of the locking arrangement relative to the housing opening and closing the slot; and
    an adjustment mechanism moving the connector relative to the housing to adjust a distance between a proximal end of the connector lumen and a distal end of the sheath.

2. The device according to claim 1, wherein the slot extends distally from a proximal end of the housing and wherein the locking arrangement is a substantially C-shaped member mounted rotatably around the proximal end of the housing.

3. The device according to claim 2, wherein the C-shaped member includes a groove formed along an inner circumference thereof and wherein the housing includes a corresponding ridge mating with the groove.

4. The device according to claim 3, wherein the ridge includes a series of spaced, projections mating with inlets formed on the groove, the mating of the projections and inlets maintaining the C-shaped member in a desired position relative to the housing.

5. The device according to claim 2, wherein the C-shaped member includes first and second ends separated from one another by a channel sized to correspond to a width of the slot.

6. The device according to claim 5, wherein a length of the channel along a circumference of the C-shaped member is no less than a width of the slot formed in the housing.

7. The device according to claim 5, including a projection contacting surface extending along a path which extends further distally as a distance from the first end of the channel increases, an end of the projection contacting surface at the first end of the channel defining a minimum distal projection of the path.

8. The device according to claim 7, wherein the path of the projection contacting surface extends a maximum distance distally at a point substantially equidistant from the first and second ends of the channel.

9. The device according to claim 1, wherein the locking arrangement includes a latch movably coupled to the housing adjacent to the slot.

10. The device according to claim 9, wherein the latch is coupled to the housing via a hinge, the latch including a tab at an end thereof opposite the hinge, the tab being insertable into a slit formed along a portion of the slit opposite the hinge.

11. The device according to claim 10, wherein the latch is slidably coupled to the housing for movement proximally and distally relative to the slot.

12. The device according to claim 11, further comprising a ratchet slide selectively locking the latch in any of a plurality of pre-defined positions.

13. The device according to claim 1, wherein the visualization device is one of a hysteroscope, a cytoscope and an endoscope.

14. A coupling arrangement for detachably coupling a visualization device to a medical device, the arrangement comprising:
   a housing including a housing lumen extending therethrough, the housing lumen being sized and shaped to slidably receive a visualization device therein and including a slot extending therethrough from an interior surface defining the housing lumen to an exterior surface thereof, the slot sized to receive therein a projection extending from the visualization device received within the housing lumen radially away from the housing lumen past the exterior surface;
   a connector movably connected to the housing to adjust a distance between a proximal end of the connector and a distal end of the device, the connector defining a connector lumen in alignment with the housing lumen and being sized and shaped to slidably receive a visualization device therein; and
   a locking arrangement securing the visualization device at a desired position within the housing.

15. The arrangement according to claim 14, wherein the locking arrangement includes a locking element coupled rotatably to a proximal end of the housing.

16. The arrangement according to claim 14, wherein the locking element is substantially C-shaped.

17. The arrangement according to claim 16, wherein the locking element includes a groove mating with a ridge formed on the housing.

18. The arrangement according to claim 14, wherein the locking element includes first and second ends separated from one another by a channel having a circumferential length substantially equal to a width of a channel formed in the housing.

19. The arrangement according to claim 15, wherein the housing includes a channel extending substantially parallel to a longitudinal axis thereof, the locking element including an engaging surface angled relative to the longitudinal axis so that rotating the locking element relative to the housing varies an extent by which the locking element overlies the channel.

20. The arrangement according to claim 14, wherein the locking arrangement includes a hinged latch.

21. The arrangement according to claim 20, wherein the hinged latch is disposed in a first slot formed along a first length of a channel formed in the housing.

22. The arrangement according to claim 21, wherein the hinged latch includes a tab at an end opposite a hinge, the tab being insertable into a second slot formed along a second length of the channel opposite the first length.

23. The arrangement according to claim 22, wherein the hinge is slidable within the first slot and the tab, when inserted into the second slot, is slidable therein.

24. The arrangement according to claim 23, wherein the tab and the second slot form a ratchet slide.

25. A coupling arrangement for detachably coupling a hysteroscope to an introducer device, the arrangement comprising:
   a housing including a hysteroscope receiving lumen extending therethrough and a ridge formed on a proximal end of the housing, the housing defining a projecting element receiving channel for receiving therewithin a projecting element of the hysteroscope, the projection element receiving channel extending through the housing from an interior surface to an exterior surface thereof to receive a projecting element extending from a hysteroscope received within the lumen radially away from the lumen past the exterior surface; and
   a locking element including a groove formed along an inner circumference thereof for mating with the ridge and rotatably coupling the locking element to the housing wherein, when in an unlocked state, a channel formed between ends of the locking element is aligned with a channel formed in the housing to allow the projecting element to be inserted into and removed from the channel and wherein, when in a locked state, the locking element closes the channel locking the projecting element within the channel.

26. The arrangement according to claim 25, wherein the locking element includes a projecting element engaging surface shaped so that, as the locking element is rotated relative to the channel, the engaging surface moves proximally and distally relative to the channel.

* * * * *